United States Patent
Argenta

(10) Patent No.: US 7,566,313 B1
(45) Date of Patent: Jul. 28, 2009

(54) CORRECTIVE INFANT HEADGEAR

(75) Inventor: Louis C. Argenta, Winston-Salem, NC (US)

(73) Assignee: American Southeast Medical Technologies, LLC, Winston-Salem, NC (US)

( * ) Notice: Subject to any disclaimer, the term of this patent is extended or adjusted under 35 U.S.C. 154(b) by 1023 days.

(21) Appl. No.: 10/460,835

(22) Filed: Jun. 12, 2003

Related U.S. Application Data

(60) Continuation-in-part of application No. 10/435,781, filed on May 12, 2003, now Pat. No. 7,153,284, and a continuation-in-part of application No. 09/479,438, filed on Jan. 7, 2000, now Pat. No. 6,592,536, which is a division of application No. 09/479,438, filed on Jan. 7, 2000, now Pat. No. 6,592,536.

(51) Int. Cl.
*A61F 5/00* (2006.01)

(52) U.S. Cl. ............................... 602/17; 128/857; 2/410

(58) Field of Classification Search .................. 602/17; 2/410, 411; 128/857; 606/204.15, 201; 607/108, 109, 110
See application file for complete search history.

(56) References Cited

U.S. PATENT DOCUMENTS

| | | | |
|---|---|---|---|
| 678,417 A | 7/1901 | Muller | |
| 1,569,877 A * | 1/1926 | Owens | ........................ 607/112 |
| 3,957,040 A | 5/1976 | Calabrese | |
| 4,354,283 A | 10/1982 | Gooding | |
| 4,446,576 A | 5/1984 | Hisataka | |
| 4,727,865 A | 3/1988 | Hill-Byrne | |
| 4,776,324 A * | 10/1988 | Clarren | ........................ 602/17 |
| 4,845,782 A | 7/1989 | Gregg | |
| 4,979,519 A | 12/1990 | Chavarria et al. | |
| 4,988,093 A | 1/1991 | Forrest, Sr. et al. | |
| 5,075,903 A * | 12/1991 | Richoux | ........................ 2/411 |
| 5,094,229 A * | 3/1992 | Pomatto et al. | ............... 602/17 |
| 5,308,312 A | 5/1994 | Pomatto et al. | |
| 5,337,420 A | 8/1994 | Haysom | |
| 5,378,042 A | 1/1995 | Daneshvar | |
| 5,511,250 A | 4/1996 | Field et al. | |
| 5,571,220 A | 11/1996 | Hall | |
| 5,637,077 A | 6/1997 | Parker | |

(Continued)

OTHER PUBLICATIONS

Danmar Products, Inc., "Special Products for Special Needs", web page at http://danmarproducts.com/index.cfm, as available via the Internet and printed Apr. 6, 2005.

(Continued)

*Primary Examiner*—Patricia Bianco
*Assistant Examiner*—Camtu Nguyen
(74) *Attorney, Agent, or Firm*—Kilpatrick Stockton LLP

(57) ABSTRACT

The present invention describes a corrective headgear for treating infants having abnormal head shape or torticollis. In an embodiment, the headgear comprises a protective shell having a curvilinear surface, wherein the curvilinear surface is positioned to overlie at least a portion of the cranium of an infant, to thereby prevent the infant from resting its head on the regions of the skull underneath the surface of the shell. In an embodiment, the headgear comprises a cloth cap that wraps around the shell to position the shell on the infant's head. Also in an embodiment, the shell comprise a convex protrusion positioned on the shell to prevent the infant from resting its head on regions of the skull protected by the headgear.

32 Claims, 4 Drawing Sheets

U.S. PATENT DOCUMENTS

| | | | |
|---|---|---|---|
| 5,887,289 | A * | 3/1999 | Theoret .......................... 2/425 |
| 5,951,503 | A | 9/1999 | Pomatto |
| 6,238,413 | B1 * | 5/2001 | Wexler .................. 606/204.15 |
| 6,381,760 | B1 | 5/2002 | Lampe et al. |
| 6,423,019 | B1 | 7/2002 | Papay et al. |
| 6,428,494 | B1 | 8/2002 | Schwenn et al. |
| 6,954,954 | B2 | 10/2005 | Stelnicki |

OTHER PUBLICATIONS

Argenta, L. et al., "An Increase In Infant Cranial Deformity With Supine Sleeping Position," *Journal of Craniofacial Surgery*, vol. 7, No. 1, Jan. 1996, pp. 5-11.

Carson, B. et al., "Technical Strategies: An Assistive Device For The Treatment Of Positional Plagiocephaly," *J. Cranial Facial Surgery*, vol. 11, Mar. 2000, pp. 177-183.

Carson, B. et al., Lambdoid Synostosis and Occipital Plagiocephaly: Clinical Decision Rules For Surgical Interventions, *Neurosurg. Focus*, vol. 2, 1997, pp. 1-10.

Clarren, S, "Plagiocephaly and Torticollis: Etiology, Natural History, and Helmet Treatment," *J. Pediatr.*, vol. 98, Jan. 1981, pp. 92-95.

Danby, P., "Plagiocephaly In Some 10-Year Old Children," *Arch. Dis. Child.*, vol. 37, May 1962, pp. 500-504.

Hellbusch, J. et al., "Active Counter-Positioning Treatment of Deformational Occipital Plagiocephaly," *Nebr. Med. J.*, Dec. 1995, pp. 344-349.

Huang, M. et al., "The Differential Diagnosis of Posterior Plagiocephaly: True Lambdoid Synostosis versus Positional Molding," *Plast. Reconstru. Surg.*, vol. 98, Oct. 1996, pp. 765-774.

Jones, B., "Occipital Plagiocephaly: An Epidemic Of Craniosynostosis," (Editorial) *BMJ*, vol. 315, Sep. 1997, pp. 693-694.

Kaiser, G., The Clinical Significance of Bilateral Synostosis of the Lambdoid Suture and the Usefulness of Its Treatment, "*Child Brain*," vol. 11, 1984, pp. 87-98.

Kane, A. et al., "Observations on a Recent Increase in Plagiocephaly Without Synostosis," *Pediatrics*, vol. 97, Jun. 1996, pp. 877-885.

Moss, S.D., "Nonsurgical, Nonorthotic Treatment of Occipital Plagiocephaly: What is the Natural History of the Misshapen Neonatal Head," *J. Neurosurg*, vol. 87, Nov. 1997, pp. 667-670.

O'Broin, E. et al., "Posterior Plagiocephaly: Proactive Conservative Management," *Br. J. Plas. Surg.*, vol. 52, 1999, pp. 18-23.

Ortega, B., "Some Physicians Do Unnecessary Surgery On Heads Of Infants—They Remold Lopsided Skull When A Corrective Band May Be All That's Needed—At Fault: Sleeping Position," *Wall Street Journal*, Feb. 23, 1996.

Persing, J. (Discussion) "The Differential Diagnosis of Posterior Plagiocephaly: True Lambdoid Synostosis versus Positional Molding," *Plast. Reconstru. Surg.*, vol. 98, Oct. 1996, pp. 775-776.

Pollack, I. et al., "Diagnosis and Management of Posterior Plagiocephaly," *Pediatrics*, vol. 99, Feb. 1997, pp. 180-185.

Pople, I. et al., "Clinical Presentation and Management of 100 Infants with Occipital Plagiocephaly," *Pediat. Neurosurg.*, vol. 25, 1996, pp. 1-6.

Rekate, H., "Occipital Plagiocephaly: A Critical Review of the Literature," *J. Neurosurg*, vol. 89, Jul. 1998, pp. 24-30.

Ripley, C., "Treatment of Positional Plagiocephaly with Dynamic Orthotic Cranioplasty," *J. Cranial Facial Surgery*, vol. 5, Jul. 1994, pp. 150-159.

Sawin, P. et al., "Quantitative Analysis of Cerebrospinal Fluid Spaces in Children with Occipital Plagiocephaly," *J. Neurosurg.*, vol. 85, Sep. 1996, pp. 428-434.

Request for Certificate of Correction mailed to USPTO on Jul. 11, 2007 for U.S. Appl. No. 10/435,781.

Notice of Allowance and Fee(s) Due mailed Aug. 8, 2006 for U.S. Appl. No. 10/435,781.

Notice of Draftsperson's Patent Drawing Review mailed Aug. 1, 2006 for U.S. Appl. No. 10/435,781.

Office Action mailed Jun. 14, 2006 for U.S. Appl. No. 10/435,781.

Office Action mailed Apr. 24, 2006 for U.S. Appl. No. 10/435,781.

Response to Telephone Interview faxed to USPTO on Jul. 28, 2006 for U.S. Appl. No. 10/435,781.

Election and Response mailed to USPTO on Jul. 11, 2006 for U.S. Appl. No. 10/435,781.

Preliminary Amendment mailed to USPTO on May 12, 2003 for U.S. Appl. No. 10/435,781.

Notice of Allowance mailed Feb. 24, 2003 for U.S. Appl. No. 09/479,438.

Office Action mailed Oct. 16, 2002 for U.S. Appl. No. 09/479,438.

Advisory Action mailed Jun. 10, 2002 for U.S. Appl. No. 09/479,438.

Office Action mailed Mar. 25, 2002 for U.S. Appl. No. 09/479,438.

Office Action mailed Jul. 20, 2001 for U.S. Appl. No. 09/479,438.

Office Action mailed Apr. 19, 2001 for U.S. Appl. No. 09/479,438.

Comments on Statement of Reasons for Allowance mailed to USPTO May 9, 2003 for U.S. Appl. No. 09/479,438.

Amendment and Reply Under 37 C.F.R. §1.116 mailed to USPTO on Jan. 16, 2003 for U.S. Appl. No. 09/479,438.

Amendment for Discussion at Interview Not For Filing mailed to USPTO on Jan. 3, 2003 for U.S. Appl. No. 09/479,438.

Preliminary Amendment and Remarks mailed to USPTO on Jul. 19, 2002 for U.S. Appl. No. 09/479,438.

Amendment and Reply Under 37 C.F.R. §1.116 mailed to USPTO on May 24, 2002 for U.S. Appl. No. 09/479,438.

Amendment and Reply Under 37 C.F.R. §1.111 mailed to USPTO on Oct. 19, 2001 for U.S. Appl. No. 09/479,438.

Reply to Election Requirement mailed to USPTO on May 8, 2001 for U.S. Appl. No. 09/479,438.

Interview Summary mailed Feb. 20, 2003 for U.S. Appl. No. 09/479,438.

Interview Summary faxed Jan. 13, 2003 for U.S. Appl. No. 09/479,438.

Interview Summary mailed Jul. 19, 2002 for U.S. Appl. No. 09/479,438.

* cited by examiner

CORRECTIVE INFANT HEADGEAR

PRIORITY CLAIM

The present invention is a continuation-in-part of U.S. patent application Ser. No. 09/479,438, filed Jan. 7, 2000, now U.S. Pat. No. 6,592,536, and U.S. patent application Ser. No. 10/435,781, filed May 12, 2003, now U.S. Pat. No. 7,153,284, which is a divisional of U.S. patent application Ser. No. 09/479,438, now U.S. Pat. No. 6,592,536. The disclosures of U.S. patent application Ser. Nos. 09/479,438 and 10/435,781 are hereby incorporated by reference in their entireties.

FIELD OF THE INVENTION

The present invention relates to orthopedics. In an embodiment, the present invention describes a headgear to be worn by an infants to correct abnormal head shape and to treat torticollis.

BACKGROUND

The cranium of a human infant is made up of frontal, parietal, temporal, occipital and other smaller bones that are separated by membranous intervals until brain growth is complete at eighteen to twenty-four months of age. Normally, the infant cranium is symmetrical in shape. However, in the condition known as plagiocephaly, the head is non-symmetrical, becoming parallelogram or rhomboid in shape. Sometimes the plagiocephalic head may correct its shape over time, but often the condition may persist, leading to facial asymmetry with functional, cosmetic, and other disabilities. If orthotic treatment is indicated, it is important to attempt correction of the deformation when the subject is less than a year old, before the sutures in the cranium have solidified.

The shape of the infant cranium is determined by multiple factors including brain growth and development, constraints placed on the skull during and after gestation, and bony abnormalities of the skull. When an infant's head is maintained in a nearly fixed position either in utero or when sleeping on a flat surface, the cranium may be progressively deformed. Thus, a condition known as occipital positional plagiocephaly or deformational plagiocephaly frequently occurs in children who sleep in a relatively constant position on their backs. For example, as a result of the American College of Pediatrics recommendation that children be placed on their back instead of on their stomach to avoid SIDS (Sudden Infant Death Syndrome), a significant number of new cranial deformities are being seen (Argenta, L. C., et al., *J. Craniofac. Surg.* 7:5-11 (1996)). In addition, many infants have craniums that are deformed either in utero or during the birth process, and sleeping on the depressed portion of the skull accentuates the deformity. Infants who are slower to develop motor activity may also develop cranial abnormalities because of their failure to move their heads frequently. Also, in some cases plagiocephaly is secondary to synostosis, a condition in which some of the skull sutures fuse too soon resulting in the skull bulging somewhere else as the brain grows.

Unfortunately, surgery is often the treatment prescribed to correct plagiocephaly of the infant skull. While plagiocephaly secondary to synostosis usually requires surgery, many deformities of the skull can be corrected with appropriate molding helmets (Argenta, L. C., et al., *J. Craniofac. Surg.* 7:5-11 (1996); Claren, S. K., et al., *J. Pediatrics* 94:43-46 (1979)). Such helmets take advantage of the pliability of the infant skull to mold the skull into a normal shape (see e.g., U.S. Pat. Nos. 4,776,324, 5,308,312, and 5,094,229). Still, these molding helmets can be constricting and uncomfortable for a small infant to wear. Also, such helmets are expensive to make and thus, are not accessible to the majority of patient who require treatment.

Thus, there is a need to develop corrective infant headgear that is comfortable for the infant to wear, and provides a gentle but effective therapy for the large majority of plagiocephalic infants. Rather than squeezing unaffected regions of the infant brain, it would be preferable to relieve the pressure from depressed areas of the skull, and thereby allow the skull to reform into its natural shape. To enable correction of the abnormality before the brain plates begin to fuse, the headgear must be comfortable enough to be worn for extended periods of time by the infant. In addition, therapeutic headgear for infants should be affordable and accessible to the many patients who require treatment.

SUMMARY OF THE INVENTION

The present invention provides a headgear which, when worn by an infant, provides for a gentle reshaping of an infant's skull. In an embodiment, the headgear comprises a hard, shell-like cap that fits over a region of the infant's skull that is soft and prone to become flat when laid upon. When wearing the cap, at least part of the infant's head rests within the concave interior of the cap and thus, is not subjected to the external surfaces that can flatten the infant's skull. Also, in an embodiment, the headgear includes a convex curvilinear protrusion on the external surface of the headgear that provides for active positioning of the infant's head. By positioning the protrusion on the headgear such that it is directly above an area on an infant's head which is abnormally flat, the headgear encourages the infant to roll away from the region of the skull under the protrusion, and to rest its head on a different region of the skull. The result is that pressure on the flat area of the skull is reduced, and pressure due to the weight of the infant's head is directed elsewhere. Also, in this embodiment, by encouraging the infant to lie on the side of the head away from the protrusion, the headgear provides a means for treating neck abnormalities such as torticollis.

Thus, in one aspect, the present invention comprises a cranial remodeling orthosis headgear comprising: a first member comprising a concave inner surface and a convex outer surface, wherein the first member overlies a part of the infant's cranium that needs to be protected from external pressure, and partially encircles the infant's cranium; and a second member for positioning the first member on the infant's head.

In another aspect, the present invention comprises a method to treat an infant having an abnormal head shape comprising the steps of:

(a) fashioning a headgear comprising a first member and a second member, wherein the first member comprises a convex exterior surface and a concave interior surface, and is shaped to cover the portion of the cranium of an infant in need of protection from external pressure, and the second member positions the first member on an infant's head;

(b) positioning the headgear on the infant's head so that the first member overlies the region of the infant's cranium in need of protection; and (c) having the infant wear the headgear for a sufficient period of time to allow the cranium to attain a clinically normal shape.

In yet another aspect, the present invention comprises a headgear for treating infants with torticollis comprising: a first member comprising a concave inner surface and a convex outer surface and having a convex protrusion attached to the outer surface; and a second member for positioning the first member over a particular region of the infant's cranium such that when the infant is wearing the headgear, the protrusion on the first member prevents the infant's head from lying on at least the part of the infant's head underlying the protrusion and encourages the infant to lie on the side of the head away from the protrusion, thereby stretching the neck muscles on the side of the head on which the protrusion is located.

In another aspect, the present invention comprises a method for treating infants with torticollis comprising the steps of:

(a) fashioning a corrective headgear comprising: (i) a first member comprising a concave inner surface and a convex outer surface and having a convex protrusion attached to the outer surface, and (ii) a second member for positioning the first member over a particular region of an infant's cranium; and (b) securing the second member on the infant's head to position the first member such that when the infant is wearing the headgear, the protrusion on the first member prevents the infant's head from lying on at least the part of the infant's head underlying the protrusion and encourages the infant to lie on the side of the head away from the protrusion, thereby stretching the neck muscles on the side of the head on which the protrusion is located.

The foregoing focuses on certain features of the invention in order that the detailed description which follows may be better understood and in order that the present contribution to the art may be better appreciated. There are, of course, additional features of the invention which will be described hereinafter and which will form the subject matter of the claims appended hereto. It is to be understood that the invention is not limited in its application to the details of construction and to the arrangement of the components set forth in the following description and drawings. The invention is capable of other embodiments and of being practiced or carried out in various ways.

DETAILED DESCRIPTION OF THE INVENTION

Figure 1:
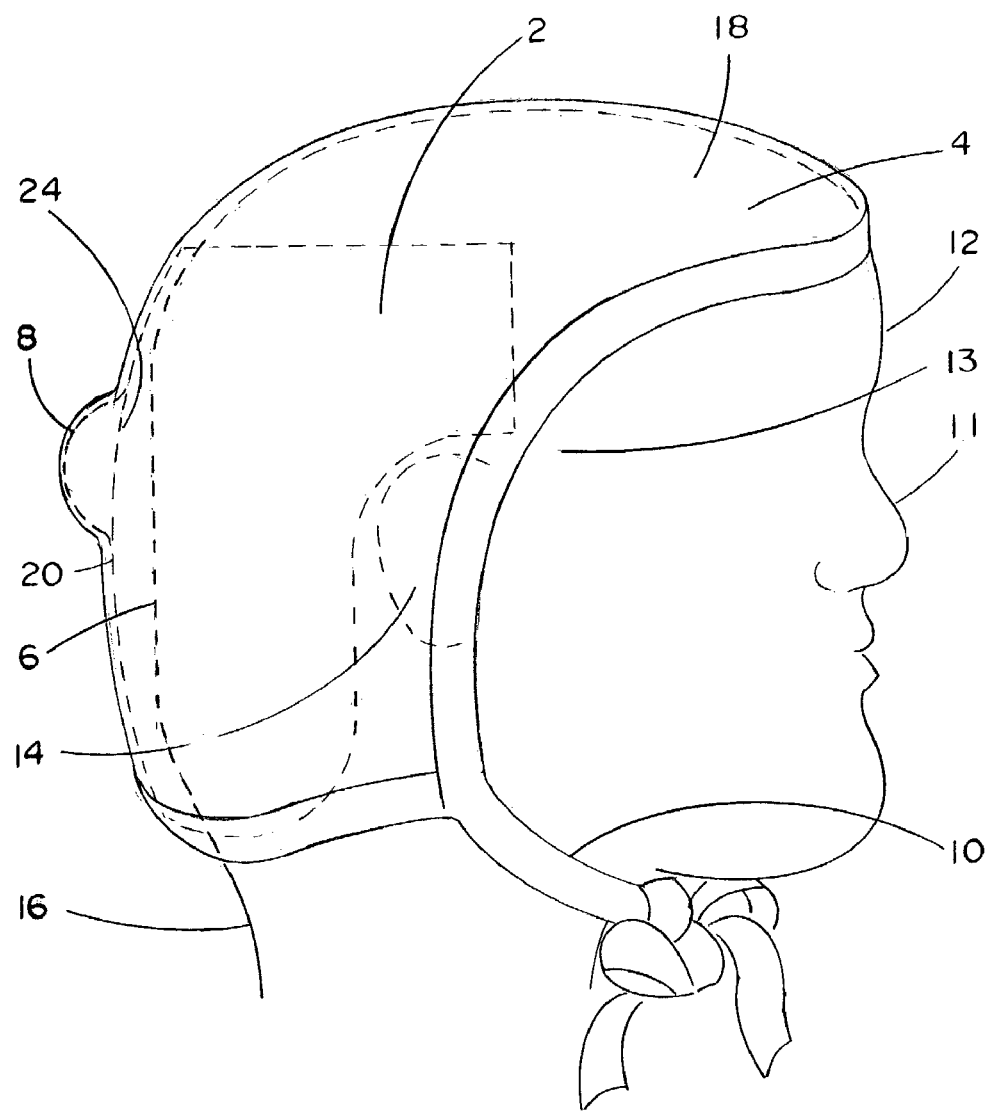
FIG. 1 is a perspective side view of an infant wearing corrective headgear in accordance with an embodiment of the present invention.

The present invention provides a light, comfortable headgear that can be worn by very young infants to treat plagiocephaly and other types of abnormalities of head shape.

Thus, in one aspect, the present invention comprises a cranial remodeling orthosis headgear comprising: a first member comprising a concave inner surface and a convex outer surface, wherein the first member overlies a part of the infant's cranium that needs to be protected from external pressure, and partially encircles the infant's cranium; and a second member for positioning the first member on the infant's head.

The present invention also comprises a method to prevent abnormalities of the skull in infants. Thus, in another aspect, the present invention comprises a method to treat an infant having a head shape abnormality comprising the steps of:

(a) fashioning a headgear comprising a first member and a second member, wherein the first member comprises a convex exterior surface and a concave interior surface, and is shaped to cover the portion of the cranium of an infant in need of protection from external pressure, and the second member and the second member positions the first member on an infant's head;

(b) positioning the headgear on the infant's head so that the first member overlies the region of the infant's cranium in need of protection; and (c) having the infant wear the headgear for a sufficient period of time to allow the cranium to attain a clinically normal shape.

The first member is designed to be worn over a region of the infant's cranium that tends to flatten upon application of external pressure. Thus, in an embodiment, the first member is designed to be worn over a region of the infant's cranium that is sufficiently soft as to become flat when the infant lies on that part of the head for extended periods of time. Preferably, the region of the cranium targeted by the present invention comprises at a least a portion of the occipital bone. In some applications, the region of the of cranium targeted by the present invention may also comprise portions of the parietal bones.

In an embodiment, the first member comprises a material that is resistant to changing shape upon application of external pressure. Also, the first member preferably comprises a material such that the first member substantially retains its shape when the infant rests its head on the concave inner surface. For example, in an embodiment, the first member comprises a high impact plastic. In alternate embodiments, the first member comprises polycarbonate, polyethylene, polypropylene, polyamide, cellular plastic, fiberglass, or the like.

The present invention recognizes that the head of an infant will expand and change shape as the infant develops. Thus, in an embodiment, the concave inner surface of the first member comprises the shape of a normal infant cranium. Thus, as pressure is released in one portion of the infant cranium, the head may expand in other regions to eventually attain a normal shape. Also, in an embodiment, the first member is shaped to provide a snug fit on regions of the head that have a normal shape. Thus, the headgear of the present invention provides support for regions of the head that are normally shaped, but provides room for flatter regions of the skull to expand as the infant brain grows.

For comfort, the interior surface of the first member may comprise padding. Preferably, the padding comprises open cell polyurethane foam, closed cell polyethylene foam, rubber, or the like.

The headgear of the present invention provides a first member that only covers a part of the infant's cranium. For example, in an embodiment, the first member is shaped as a hard shell that covers the back of the infant's head. Because the shell does not completely encircle the infant's cranium, it can slide out of position, or fall completely off the infant's head unless it is secured in place. Thus, a second member is provided to securely position the first member on the infant's head.

In an embodiment, the second member secures the first member on the infant's head. Preferably, the second member secures the first member on the infant's head such that at least part of the inner surface of the first member is immediately adjacent to the infant's head.

The second member may completely cover the first member, or it may be a small strap or other attachment fixed to the first member. For example, in an embodiment, the second member at least partially wraps around the outer surface of the first member. Preferably, the second member comprises a cloth cap or bonnet. In an embodiment, the cap comprises a pocket into which the first member is inserted. Also the second member may comprise a chin strap to secure the first member on the infant's head. Generally, the chin strap allows the headgear to be positioned to fit snugly on the infant's head, so that space between first member and region(s) on the infant's skull that are not flat is minimized. Thus, the headgear does not have to be custom fitted to the infant's skull.

In an embodiment, the headgear of the present invention utilizes an additional means to prevent the infant from resting its head on a flat region of the skull (or a soft region of the skull that is easily flattened). Thus, in an embodiment, the present invention comprises a convex protrusion positioned on the outer (exterior) surface of the first member. In an embodiment, the convex protrusion prevents the infant's head from lying on at least a part of the first member underlying the protrusion, and encourages the infant's head to lie on other regions of the head.

In an embodiment, the protrusion is curvilinear shape. Also in an embodiment, the convex protrusion comprises a hemisphere, a truncated cone, a trapezoid, an inverted cup, or an arched band.

In an embodiment, the convex protrusion is directly affixed to the outer surface of the first member. Various methods may be used to attached the convex protrusion to the first member. Thus, in an embodiment, the convex protrusion is directly affixed to the outer surface of the first member using fasteners such as screws, bolts, or the like. To increase flexibility in positioning the protrusion on the first member, a method of attaching the protrusion which is independent of the placement of fasteners on the first member can be employed. For example, in an embodiment, the convex protrusion comprises non-invasive attachment to said first member. In alternate embodiments, the non-invasive attachment comprises adhesive, snaps, VELCRO®, or thermal molding.

In an embodiment, the protrusion is of a material such that it is able to gently push the infant's head into a position so that the infant does not lie directly on the protrusion, but rests its head on a part of the skull away from the protrusion. Thus, the protrusion may be of a material that holds its shape to an extent such that when the infant lies directly on the protrusion, there is some discomfort. The protrusion should not be so extensive, however, as to force the infant's head into an awkward position or to restrict motion excessively. In addition, the protrusion should be of a material that is light enough not to put an undue strain on the infant's neck muscles.

For example, in an embodiment, the convex protrusion attached to the first member comprises a spring-like material that substantially holds its shape when the infant rests its head thereon. Preferably, the spring-like material comprises foam, such as a polyalcohol-based foam. Alternatively, the protrusion may be made of a lightweight plastic (such as polyethylene or polypropylene), or an inflatable bladder.

The present invention also describes headgear and methods for the treatment of torticollis. Torticollis is a condition in which the muscles of one portion of the neck are excessively tight. Usually the infant favors the affected side of the neck. This results in the head being twisted to one side, which can produce a secondary depression and asymmetry of the skull. Such children require frequent exercises to mobilize the head to the opposite side.

Thus, in yet another aspect, the present invention comprises a headgear for treating infants with torticollis comprising: a first member comprising a concave inner surface and a convex outer surface and having a convex protrusion attached to the outer (exterior) surface; and a second member for positioning the first member over a particular region of the infant's cranium such that when the infant is wearing the headgear, the protrusion on the first member prevents the infant's head from lying on at least the part of the infant's head underlying the protrusion and encourages the infant to lie on the side of the head away from the protrusion, thereby stretching the neck muscles on the side of the head on which the protrusion is located.

In another aspect, the present invention comprises a method for treating infants with torticollis comprising the steps of:

(a) fashioning a corrective headgear comprising: (i) a first member comprising a concave inner surface and a convex outer surface and having a convex protrusion attached to the outer surface, and (ii) a second member for positioning the first member over a particular region of an infant's cranium; and (b) securing the second member on the infant's head to position the first member such that when the infant is wearing the headgear, the protrusion on the first member prevents the infant's head from lying on at least the part of the infant's head underlying the protrusion and encourages the infant to lie on the side of the head away from the protrusion, thereby stretching the neck muscles on the side of the head on which the protrusion is located.

Thus, the corrective headgear of the present invention uses a protruding element on the headgear to force the head to the side away from the torticollis. The convex protrusion is designed to encourage the infant to rest its head in such a manner such that the neck muscles that are excessively tight due to torticollis are stretched as the infant sleeps. The convex protrusion positioned on the outer surface of the first member may comprise a hemisphere, a truncated cone, a trapezoid, an inverted cup, an arched band, or other type of convex shape. Progressive increases in size of the protruding element can be employed as the neck muscles become increasingly relaxed.

In an embodiment, the first member comprises high impact plastic. Preferably, the exterior surface of the first member comprises polycarbonate, polyethylene, polypropylene, polyamide, cellular plastic, or fiberglass.

Also in an embodiment, the interior surface of the first member comprises padding. Preferably, the padding comprises open cell polyurethane foam, closed cell polyethylene foam, rubber, or the like.

In an embodiment, the second member secures the first member on the infant's head. Preferably, the second member secures the first member on the infant's head such that at least part of the inner surface of the first member is immediately adjacent to the infant's head.

In an embodiment, the second member at least partially wraps around the outer surface of the first member. For example, the second member may comprise a cloth cap that wraps around the first member. Also preferably, the second member may comprise a cap having a pocket into which the first member is inserted. Alternatively and/or additionally, the second member may comprise a chin strap to secure the first member on the infant's head.

Various methods may be used to attached the convex protrusion to the first member. Thus, in an embodiment, the convex protrusion is directly affixed to the exterior surface of the first member using fasteners such as screws, bolts, or the like. Alternatively, the convex protrusion comprises non-invasive attachment to the first member. For example, adhesive, snaps, VELCRO®, or thermal molding may be used.

In an embodiment, the protrusion is of a material such that it is able to gently push the infant's head into a position so that the infant does not lie directly on the protrusion, but rests its head on a part of the skull away from the protrusion. Thus, the protrusion may be of a material that holds its shape to an extent such that when the infant lies directly on the protrusion, there is some discomfort. The protrusion should not be so extensive, however, as to force the infant's head into an awkward position or to restrict motion excessively.

In addition, the protrusion should be of a material that is light enough not to put an undue strain on the infant's neck muscles. For example, in an embodiment, the convex protrusion attached to the first member comprises a spring-like or spongy material that substantially holds its shape when the infant rests its head thereon. Preferably, the spring-like material comprises foam, such as a polyalcohol-based foam. Alternatively, the protrusion may be made of a lightweight plastic (such as polyethylene), or an inflatable bladder.

Thus, the present invention describes a headgear to be worn by infants for the treatment of abnormal head and neck conditions. As used herein, treatment includes the full spectrum of treatments for a given disorder from which the patient is suffering, including alleviation of one, or most, or all, of the symptoms resulting from that disorder, to an outright cure. Also, although, the headgear of the present invention is not routinely used as a prophylactic, it may be used to prevent the formation of abnormal head shape in infants. For example, the headgear of the present invention could be placed on the head of an infant such that when the infant is placed to sleep on its back, the soft region at the back of the skull does not flatten.

As used herein, abnormal head shape comprises a head that does not conform to the clinically accepted standards for normal head shape for infants. Thus, as used herein, a normal head shape comprises a head that comprises two back quadrants and two front quadrants that are substantially symmetrical with respect to each other. Thus, a clinically normal head has a cross-section in which the two back quadrants are substantially symmetrical with respect to each other, the two front quadrants are substantially symmetrical shaped with respect to each other, and the front and back of the head are substantially symmetrical with respect to each other. For example, known standards based on CT scans of infant heads are available and provide a range of shapes for infant heads. Preferably, a normally shaped head falls in the shape range found for 80% of infants. For example, a set of measurements comprising the various range of sizes and shapes for infant heads is found in Lusted L. B., and Keats, T. E., Atlas of Roentgenographic Measurement, Chicago: Year Book Publishers, (1959).

Certain regions of the infant cranium are quite soft and will become flat if the infant rests on that portion of the skull for extended periods of time. Thus, the present invention provides a means to prevent a flat external surface from pressing on these soft regions of the skull. As pressure is relieved from these regions of the skull, the developing infant brain pushes the bones outward, thus re-modeling the head back to the correct shape.

In an embodiment, the headgear partially encircles the cranium. As used herein, partially encircles includes less than completely encircling. Assuming a complete circle comprises 360 degrees, embodiments of the present invention comprise arcuate members less than 360 degrees around, as for example, a shell having an outer circumference of about 130 to 180 degrees around. Particular embodiments of the present invention comprise arcuate members that partially encircle an infant's cranium. In certain embodiments, the first member encircles 20 to 270 degrees around an infant's cranium. Or, the first member may encircle 60 to 230 degrees around an infant's cranium. Or, the first member may encircle 90 to 180 degrees around an infant's cranium. In an embodiment, the first member encircles about 150 degrees around an infant's cranium.

Thus, in an embodiment, the present invention provides a hard shell or cap which has an convex inner surface. When the infant lies on the convex inner surface of the cap, the surface maintains its shape such that there is no flat surface against the infant's head.

The headgear of the present invention is designed to be unobtrusive and thereby allow the infant to move its head freely when lying down, sitting, or walking. In addition, the headgear of the present invention does not squeeze the infant's head in any manner. Instead, the headgear provides a concave surface that does not push against the skull, but allows the infant's head to expand to the proper shape.

Alternatively, in an embodiment, the headgear of the present invention comprises a convex protrusion that is attached to the first member. In this embodiment, the protrusion is used to encourage the infant to roll its head away from the affected area. In the case of a flattened skull, the affected area is the flattened region of the skull. In the case of torticollis, the affected area is the side of the neck in which the muscles are excessively contracted.

Previously, infants having abnormally shaped heads have been treated using helmets to be worn by the infant. There are essentially two types of corrective infant helmets. An active helmet is a device that places an active constricting force on the skull to force it to grow in a more normal fashion. In general, active helmets must be custom fitted, require significant amounts of time for fabrication, and must be changed frequently as the infant head changes in shape and increases in size. As a result, therapy employing active helmets requires multiple clinic visits and may be too costly for most patients. In addition, placing a constricting force on the growing brain is not considered physiological by most physicians.

For example, a helmet to correct brachycephalic cranial abnormalities is described in U.S. Pat. No. 5,308,312. The helmet described in U.S. Pat. No. 5,308,312 is designed to address a unique form of abnormal head shape, and for maximum effectiveness, must be fabricated from an impression of the individual subject's head. Also, a cranial remodeling band using active molding to treat plagiocephaly is described in U.S. Pat. No. 5,094,229. The technology employs active molding in that it applies corrective forces to those regions of the cranium which protrude. Still, effective therapy requires that the orthosis be individualized for each subject, with a series of bands required for each infant.

Passive helmets or soft shell helmets attempt to take pressure off of the deformed portion of the skull to allow the developing infant brain to grow in a more normal fashion. Thus, in contrast to active molding, passive helmets provide for a more gradual and physiological correction of skull shape. For example, a graded series of passive helmets for treatment of infant plagiocephaly are described in U.S. Pat. No. 4,776,324. The helmet fully encloses the head, and is designed such that it is slightly larger than the patient's skull. Still, the technology requires a graded series of helmets to be used as the infant develops.

In contrast to helmets described previously, the present invention describes a headgear that employs passive therapy, but covers only the portion of the head to be protected or remodeled. Thus, the headgear of the present invention is less cumbersome than the full helmets used previously. Also, the headgear of the present invention is easy to put on the infant, and may be worn for extended periods when the infant is awake as well as when the infant is asleep.

For example, a typical headgear of the present invention is constructed of a plastic (i.e., polyethylene) first member approximately 2-4 mm thick and molded to fit on the back of the head of an infant. For comfort, foam padding may be added on the inside of the first member. The first member is shaped to fit upon the part of the infant's head that needs to be treated. In an embodiment, the first member is designed to fit over the back of the infant's head. Various shells can be made to fit infants having heads of differing sizes. The headgear of the present invention may be used for infants ranging in age from 1 month to 2 years. More preferably, however, the headgear of the present invention is used for infants ranging in age from 3 to 4 months to about 14 to 16 months.

The headgear of the present invention also comprises a second member attached to the first member for positioning the first member on the infant's head. For example, the second member may comprise straps, such as chin straps. In an embodiment, the chin straps may be directly attached to the first member, as for example, using pins or other type of fastener. Alternatively, the second member may comprise a cap that wraps around the first member and sits on the head to secure the first member in place. In an embodiment, the cap has chin straps to hold the cap and first member in place. For example, the cap may be designed as a bonnet that is attached to the first member using adhesive tape or VELCRO® fasteners. Alternatively, the second member may comprise a cap having a sleeve into which the first member is inserted.

The first member provides a concave inner surface against the infant's head. Thus, when the infant rests its head upon the first member, the head of the infant will lie on a concave surface, rather than a flat surface. In this way, the infant's head is not subjected to external forces that can lead to flattening of the infant's skull. Instead, the infant head is supported by resting on the inner surface of the first member. The first member may be designed so that the inner surface mirrors the shape of a normal cranium. Thus, the parts of the infant's head that are correctly shaped will lie directly adjacent to the first member, whereas the parts of the infant's head that are flat will be free of any external force pressing against the cranium. In this way, the sections of the infant's head that comprise harder bone and that are correctly shaped are supported by the first member, whereas flattened regions of the cranium are not subjected to resting on a flat surface.

Alternatively, the headgear of the present invention may comprise a convex protrusion attached to the first member and positioned such that the protrusion prevents the infant's head from lying on at least a part of the first member underlying the protrusion, and encourages the infant's head to lie on other regions of the head. Generally, the protrusion is positioned over the region of the infant's head that is flat. In this way, the infant is encouraged to rest its head on a different part of the cranium than the part of the cranium that is flat, or that comprises soft bone.

Referring now to FIG. 1, in an embodiment, the headgear of the present invention includes a first member 2, having a convex exterior surface 20 and a concave inner surface 24, that is shaped to cover the back of the head 6. Thus, first member 2 may be shaped as a convex shell. When positioned on the infant's head, the first member may be designed to leave a significant portion of the infant's head exposed, including the frontal 12 and temporal 13 regions. In an embodiment, first member 2 does not cover the ears 14, face and nose 11, or extend to the neck 16. It can be seen that in the case where the back of the infant's head 6 is flat, the first member 2 retains its shape to present a concave inner surface to the back of the head 6.

Still referring to FIG. 1, it can be seen that the second member may comprise a cap or bonnet 4 that wraps around the first member 2. In an embodiment, the cap 4 extends beyond first member 2, to cover the cephalad most cranium 18. Alternatively, the second member may extend only as far as first member 2, or may cover only a portion of first member 2. For example, in an embodiment, the second member may comprise chin straps directly attached to first member 2, without any type of external cap. For example, pins may be used to attached chin straps directly to the first member 2. Alternatively, the second member may comprise a cap 4 and chin straps 10.

Also shown in FIG. 1, is the optional convex protrusion 8 which may be attached to the first member 2. Thus, in an embodiment, protrusion 8 prevents the infant's head from lying on at least a part of the first member 2 underlying the protrusion 8, and thus, prevents the infant from lying its head on a flat region 6 of the cranium.

Figure 2:
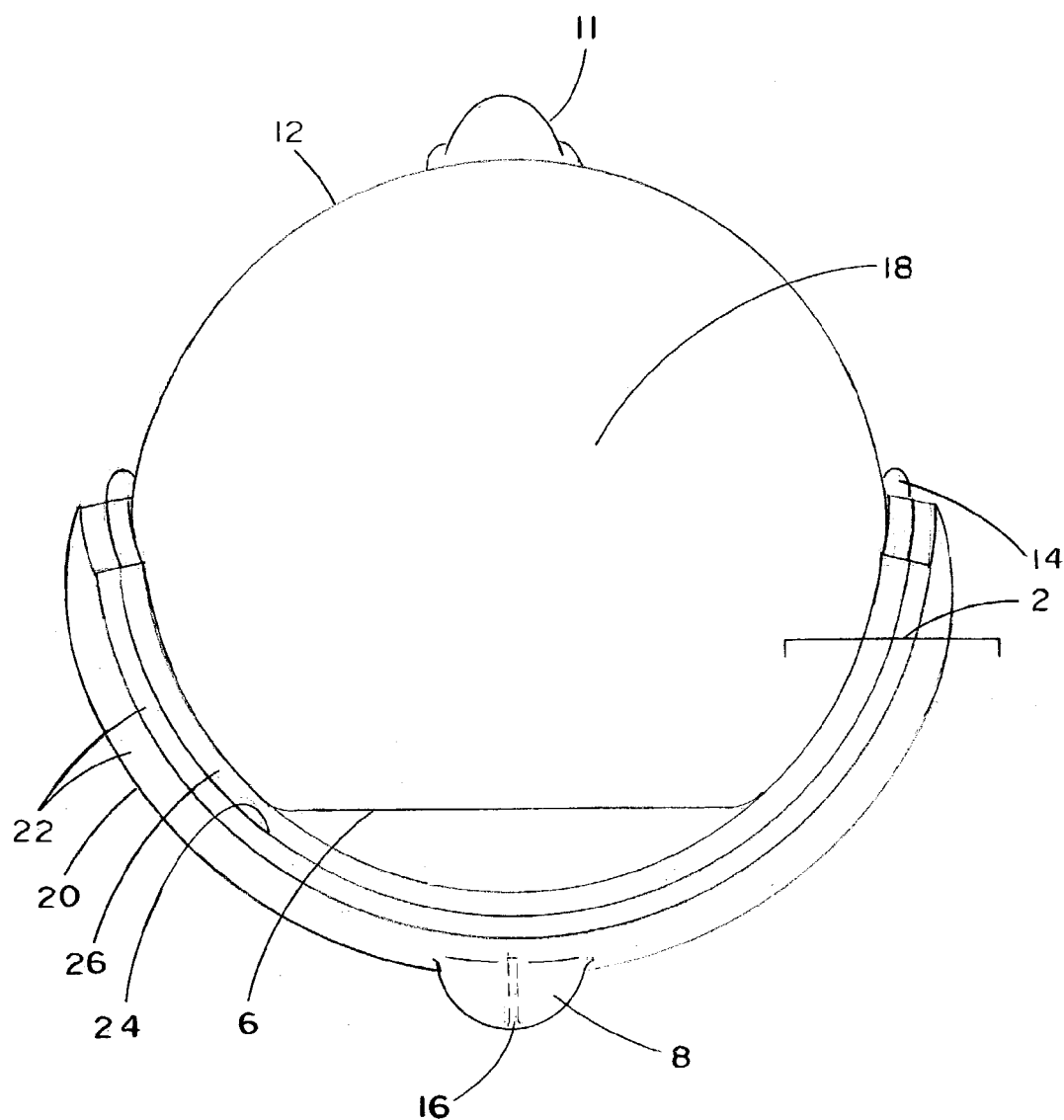
FIG. 2 is a perspective top view of the first member of the corrective headgear positioned on an infant's head in accordance with an embodiment of the present invention.

FIG. 2 shows a top view of the first member 2 as seen in position on an infant's head to cover the back 6 of the head, but not the front 12 of the head. Thus, in an embodiment, first member 2 comprises a convex exterior surface 20 comprising a shell 22 of high impact plastic, which is lined on the inner concave surface 24 with foam rubber 26. Although first member 2 may cover the ears 14, it is generally more comfortable for the wearer if the ears are not covered by the hard shell. Also shown is the optional convex protrusion 8. In an embodiment, the convex protrusion 8 is attached to the outer surface 20 of the first member 2 by a bolt or some other type of fastener 16. Alternatively, the protrusion 8 may be attached to the convex member by an adhesive such as sticky tape or VELCRO®.

Figure 3:
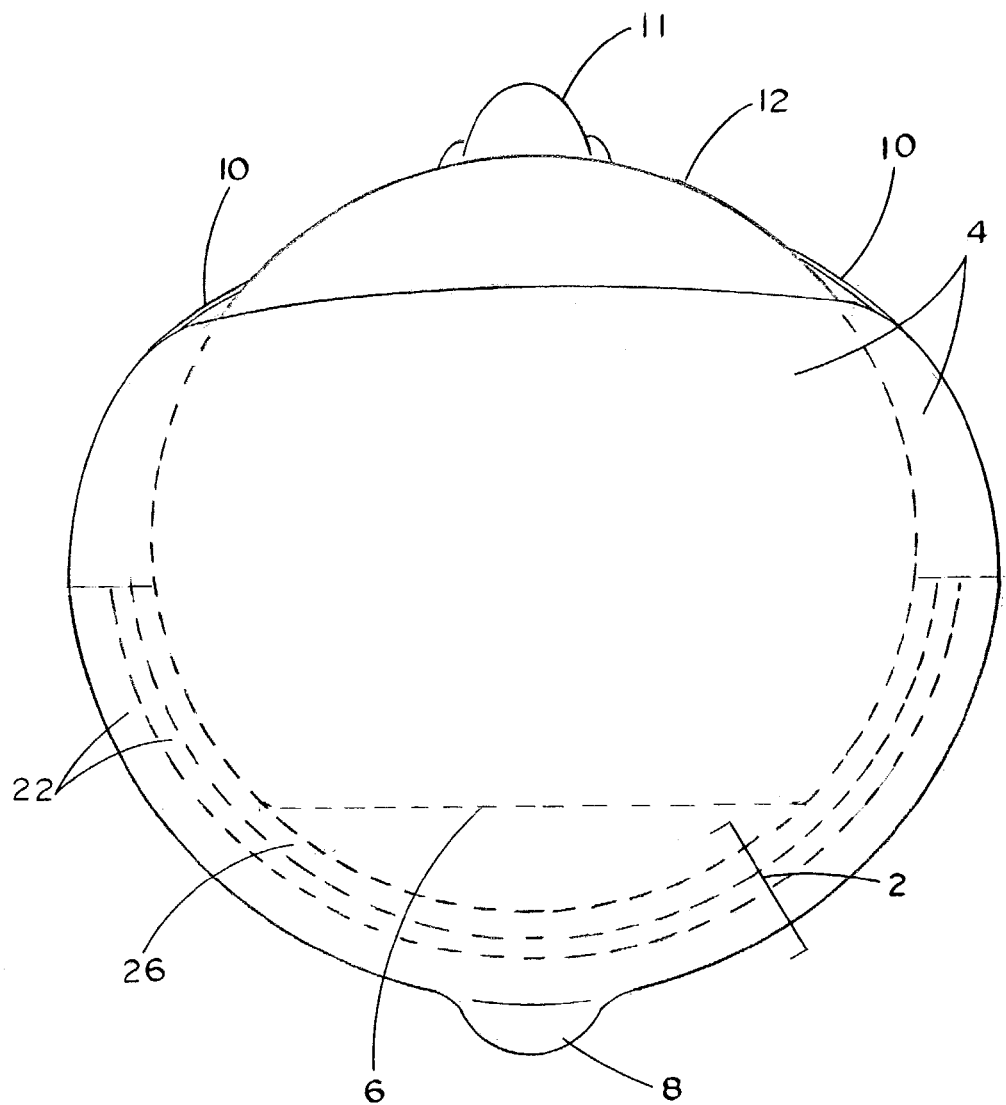
FIG. 3 is a perspective top view of the first and second members of the corrective headgear positioned on an infant's head in accordance with an embodiment of the present invention.

FIG. 3 shows a top view of the headgear of the present invention including the first member 2 and the second member 4 as positioned on the head of an infant. Thus, in an embodiment, the headgear of the present invention comprises a simple bonnet which is easily put on the infant's head. The bonnet may be positioned to have the first member 2, and optionally, the convex protrusion 8, overlie a region of the skull which has been flattened 6. In an embodiment, chin straps 10 are used to position and secure the bonnet on the infant's head.

Figure 4:
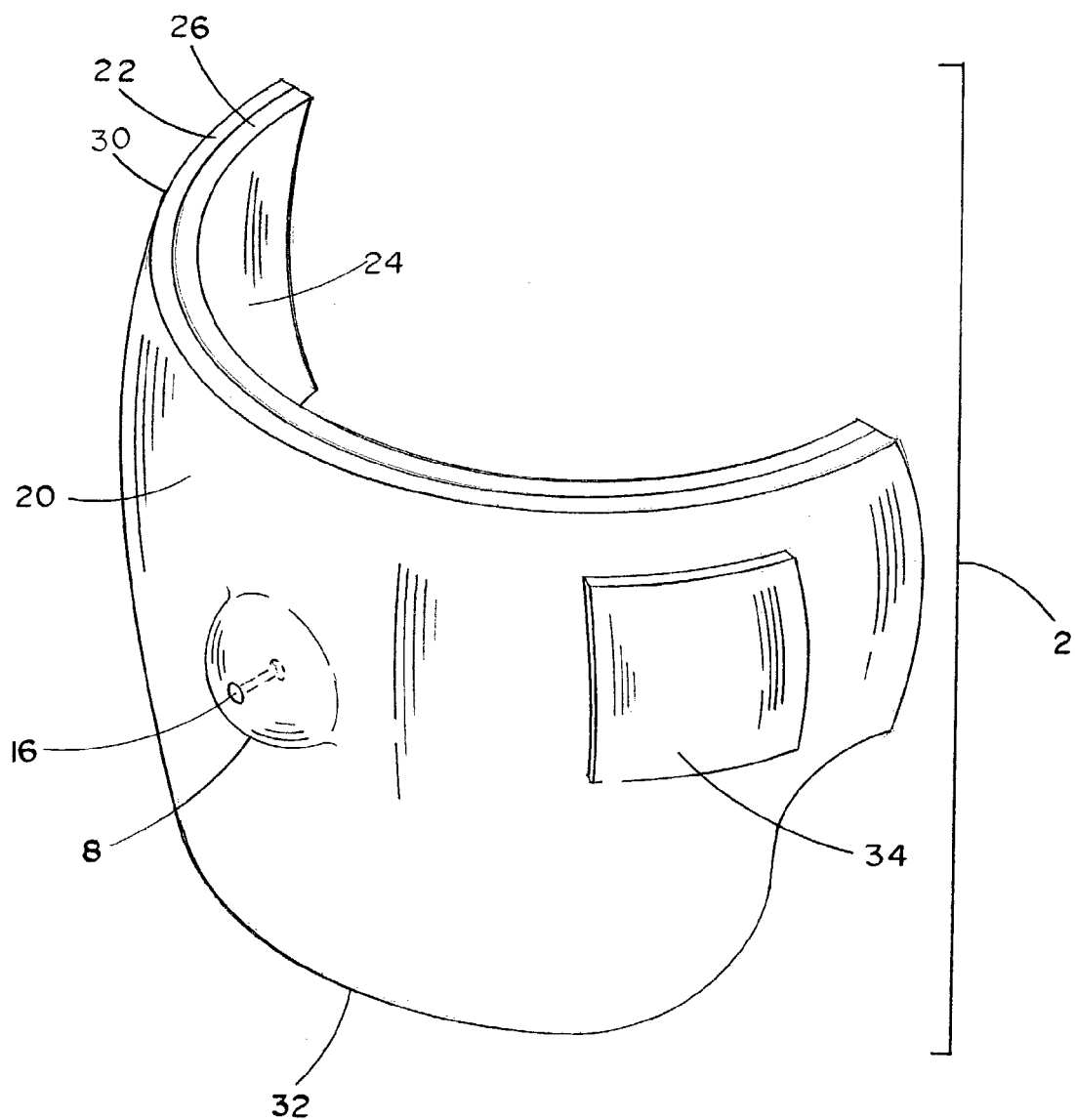
FIG. 4 is a perspective side/rear view of the first member of the headgear and the convex protrusion in accordance with an embodiment of the present invention.

FIG. 4 shows a perspective view of the first member 2 in accordance with an embodiment of the present invention. Thus, it can be seen that in an embodiment, first member 2 is a shell-like structure 22, having a convex outer surface 20, and shaped to enclose a majority of the back of an infant's head. The shell has an inner concave surface 24 designed to mirror the shape of a normal infant head, and which is lined with padding 26 for comfort. The top 30 of the first member 2 may be cut to allow almost the entire top of the infant's head to remain uncovered. Alternatively, the first member may comprise a top section, to protect the top of the head as well as the shell which covers the back of the head. The bottom 32 of the first member 2 is preferably designed to end above the neck when worn by the infant. Again shown is the optional convex protrusion 8 attached via a fastener 16 to the first member.

Also shown, is a fastener 34, preferably made of VELCRO® or sticky tape, for attaching a second member cap 4 to the first member.

Thus, the benefits of the headgear of the present invention include a gentle therapy for the treatment of skull abnormalities. The headgear does not squeeze the patient's head, but simply provides a concave surface on which the infant may rest its head. Thus, when the infant lies on its back, the head of the infant will lie on a concave surface, rather than a flat surface. In this way, the infant's head is not subjected to the external force that can lead to flattening of the infant's skull. Instead, the infant head is supported by resting on the inner surface of the first member.

Alternatively, the headgear may comprise a convex protrusion position that encourages the infant to sleep on the non-depressed region of the skull. Except for preventing the infant from lying on the affected area, this embodiment allows for universal movement of the head.

Because the headgear only covers a portion of the infant's head, it is relatively small, and thus, does not add significant weight or restrict the infant with respect to turning and lifting its head. Also, because of its simple design, the headgear may be provided in a range of sizes that will fit most infants as they grow. As only the sides of the first member need to fit closely on the infant's head, the headgear of the present invention does not have to be custom-molded for each infant. Instead, the second member cap may be used to secure the first member snugly on the infant's head.

The adjustable nature of the headgear of the present invention obviates the need for molding the headgear to be an exact fit of the infant's head. Custom-fitting of orthotic helmets often requires sedating the infant, and because of the required technology involved, can add greatly to the cost of orthotic helmets. Additionally, custom-fitting significantly increases the interval between diagnosis and effective treatment. In the case of infant development, the window for treatment is limited to infants between 3-4 months to about 14 months old. Thus, delays in the onset of treatment may significantly reduce the effectiveness of the treatment. In light of the fact that more and more infants are being denied appropriate treatment because of the cost of custom-fitting helmets, the present invention provides a valuable alternative.

Example

An embodiment of the headgear of the present invention was manufactured essentially as follows. To fashion the exterior shell of the first member, a flat piece of polyethylene plastic was shaped to conform to the back of a skull. The first member may be produced from any type of material that will retain its shape when the infant rests its head on it, but that is not so hard or heavy that it will create undue strain on the infant's neck muscles.

Shells of various sizes are easily manufactured based on the standard dimensions of the developing infant head. To accommodate changes in the patient's skull size, first members are prefabricated in several sizes such that the resultant shells encompass the majority of skulls for infants between the ages of 2 months to about 14 to 16 months. Because infants' skulls follow a bell shaped growth curve, a relatively well-defined and narrow range of first members will overlap the majority of infant head sizes. Custom shells can be made for exceptional skulls.

Thus, first members of varying size were made using templates which had been generated based upon measurements taken from a series of normal infant skulls or CAT scans. After the shell hardened into its final shape, padding was glued to the inner surface. Apertures were drilled through the first member (and padding) to provide a means for attaching a convex protrusion to the first member. Holes made in the padding were at least partially resealed with padding for comfort. This allowed for fasteners threaded through the apertures to be used to attach a convex protrusion to the first member.

Alternatively, fasteners for the convex protrusion may be glued onto the external surface, or threaded through the apertures on the first member. Also, VELCRO® strips can be affixed to the exterior of the first member. Thus in one embodiment, VELCRO® was used to attach a foam convex protrusion to the first member.

Convex protrusions of a size and shape as to prevent the infant from lying on the part of the head under the protrusion were made. In a working embodiment, a polyalcohol foam hemispherical protrusion about 1.25 inches in diameter was used as the protrusion. The size of the protrusion may depend on the condition being treated. Thus, the degree of protrusion may vary depending upon the severity of the deformity and the child's stage of neuromuscular development.

To make the second member, alternative bonnets were developed that wrapped around the first member to allow the first member to be secured on the infant's head. Thus, in an embodiment, a cotton/polyester bonnet shaped to cover the back of the head (and first member), and at least a part of the top of the infant's head, was wrapped around the first member shell. The bonnet was stuck to the shell using double-sided sticky tape. In another embodiment, a bonnet was made having a pocket into which the shell could be inserted. The bonnets included chin straps attached to the front lower portion of the bonnet which allowed the bonnet (and first member shell) to be securely positioned on the infant's head.

Although the bonnets of the present invention may be easily taken on or off, they may be worn for extended periods of time. Thus, the bonnets may be worn 24 hours a day, and only need to be removed for bathing.

With respect to the descriptions set forth above, optimum dimensional relationship of parts of the invention (to include variations in size, materials, shape, form, function and manner of operation, assembly and use) are deemed readily apparent and obvious to those skilled in the art, and all equivalent relationships to those illustrated in the drawings and described in the specification are intended to be encompassed herein. The foregoing is considered as illustrative only of the principal of the invention. Since numerous modifications and changes will readily occur to those skilled in the art, it is not intended to limit the invention to the exact construction and operation shown and described, and all suitable modifications and equivalents falling within the scope of the appended claims are deemed within the present inventive concept.

It is to be further understood that the phraseology and terminology employed herein are for the purpose of description and are not to be regarded as limiting. Those skilled in the art will appreciate that the conception on which this disclosure is based may readily be used as a basis for designing the structures, methods and systems for carrying out the several purposes of the present invention. The claims are regarded as including such equivalent constructions so long as they do not depart from the spirit and scope of the present invention.

What is claimed is:

1. A cranial remodeling orthosis headgear for use by an infant comprising:
   a first member comprising a concave inner surface and a convex outer surface, wherein the first member is comprised of an arcuate member having an outer circumference of less than 360 degrees, wherein the concave inner surface spans the entire arcuate member, and wherein the first member is shaped to only partially encircle the infant's cranium so as to cover at least a portion of the back of the infant's cranium including a portion of the occipital bone but to leave the frontal bone substantially uncovered;

a convex protrusion attached to the convex outer surface of the first member, wherein the convex protrusion covers only a portion of the convex outer surface and is positioned so that when the headgear is worn by the infant and the infant is lying on a surface, the protrusion encourages the infant's head to lie on a portion of the cranium other than the part of the cranium underlying the protrusion; and a second member for positioning the first member on the infant's head, wherein the second member comprises a cloth cap.

2. The headgear of claim 1, wherein the first member is designed to be worn over a region of the infant's cranium that is sufficiently soft as to become flat upon application of external pressure due to the infant lying on that region of the head for extended periods of time.

3. The headgear of claim 1, wherein the protrusion comprises a high impact plastic.

4. The headgear of claim 1, wherein the region of the cranium protected by the first member comprises at least a part of the parietal bones.

5. The headgear of claim 1, wherein the concave inner surface of the first member comprises the shape of a normal infant cranium.

6. The headgear of claim 1, wherein the first member comprises a material such that the first member substantially retains its shape when the infant rests its head on the concave inner surface.

7. The headgear of claim 1, wherein the first member comprises high impact plastic.

8. The headgear of claim 1, wherein the outer surface of the first member comprises polycarbonate, polyethylene, polypropylene, polyamide, cellular plastic, or fiberglass.

9. The headgear of claim 1, wherein the inner surface of the first member comprises padding.

10. The headgear of claim 9, wherein the padding comprises open cell polyurethane foam, closed cell polyethylene foam, or rubber.

11. The headgear of claim 1, wherein the second member secures the first member on the infant's head.

12. The headgear of claim 11, wherein the second member secures the first member on the infant's head such that at least part of the inner surface of the first member is immediately adjacent to the infant's head.

13. The headgear of claim 1, wherein the second member at least partially wraps around the outer surface of the first member.

14. The headgear of claim 1, wherein the first member is shaped to cover a part of an infant's cranium that needs to be protected from external pressure.

15. The headgear of claim 1, wherein the cap comprises a pocket into which the first member is inserted.

16. The headgear of claim 1, wherein the second member comprises a chin strap to secure the first member on the infant's head.

17. The headgear of claim 1, wherein the first member comprises an outer circumference that ranges from about 90 degrees to about 150 degrees.

18. The headgear of claim 1, wherein the first member comprises an outer circumference that ranges from about 130 degrees to about 180 degrees.

19. The headgear of claim 1, wherein the protrusion is curvilinear shape.

20. The headgear of claim 1, wherein the protrusion comprises a hemisphere, a truncated cone, a trapezoid, an inverted cup, or an arched band.

21. The headgear of claim 1, comprising noninvasive attachment of the protrusion to the first member.

22. The headgear of claim 1, wherein the protrusion is attached to the first member using adhesive, snaps, hook and loop fasteners, or thermal molding.

23. The headgear of claim 1, wherein the protrusion attached to the first member comprises a spongy or spring-like material.

24. The headgear of claim 23, wherein the spring-like material comprises foam.

25. A method to treat an infant having an abnormal head shape comprising the steps of:

(a) fashioning a headgear comprising a first member and a second member, wherein the first member comprises a convex exterior surface and a concave interior surface, wherein the first member is comprised of an arcuate member having an outer circumference of less than 360 degrees, wherein the concave inner surface spans the entire arcuate member, wherein the first member is shaped to only partially encircle the infant's cranium, and the second member positions the first member on the infant's head, and wherein the second member comprises a cloth cap;

(b) attaching a convex protrusion to the outer surface of the first member such that when the first member is positioned on the infant's head, the convex protrusion covers only a portion of the convex outer surface and is positioned so that when the headgear is worn by the infant and the infant is lying on a surface the protrusion encourages the infant's head to lie on a different part of the cranium other than the part of the cranium underlying the protrusion;

(c) positioning the headgear on the infant's head so that the first member overlies a region of the infant's cranium in need of protection wherein the positioning comprises the headgear covering a portion of the occipital bone and leaving the frontal bone substantially uncovered; and (d) having the infant wear the headgear for a sufficient period of time to allow the cranium to attain a clinically normal shape.

26. The method of claim 25, wherein the second member at least partially wraps around the outer surface of the first member.

27. The method of claim 25, wherein the cap comprises a pocket into which the first member is inserted.

28. The method of claim 25, wherein the second member comprises a chin strap to secure the first member on the infant's head.

29. The method of claim 25, wherein the first member comprises an outer circumference that ranges from about 130 degrees to about 180 degrees.

30. The method of claim 25, wherein the protrusion is curvilinear shape.

31. The method of claim 25, wherein the first member comprises high impact plastic.

32. The method of claim 25, wherein the inner surface of the first member comprises padding.

* * * * *

UNITED STATES PATENT AND TRADEMARK OFFICE
CERTIFICATE OF CORRECTION

| | | |
|---|---|---|
| PATENT NO. | : 7,566,313 B1 | Page 1 of 1 |
| APPLICATION NO. | : 10/460835 | |
| DATED | : July 28, 2009 | |
| INVENTOR(S) | : Argenta | |

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 1023 days.

Delete the phrase "by 1023 days" and insert -- by 1515 days --

Signed and Sealed this

Twenty-seventh Day of April, 2010

David J. Kappos
*Director of the United States Patent and Trademark Office*